(12) United States Patent
Ikeuchi et al.

(10) Patent No.: US 7,633,604 B2
(45) Date of Patent: *Dec. 15, 2009

(54) SAMPLE ANALYZER AND COMPUTER PROGRAM PRODUCT

(75) Inventors: Yoshiro Ikeuchi, Kobe (JP); Shinichiro Oguni, Akashi (JP); Daigo Fukuma, Kobe (JP); Masanori Imazu, Takasago (JP); Jo Lissen, Kerkrade (NL)

(73) Assignee: Sysmex Corporation, Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/204,736

(22) Filed: Sep. 4, 2008

(65) Prior Publication Data

US 2009/0076736 A1 Mar. 19, 2009

Related U.S. Application Data

(63) Continuation of application No. 11/844,522, filed on Aug. 24, 2007, now Pat. No. 7,450,223, which is a continuation of application No. 11/076,048, filed on Mar. 10, 2005, now Pat. No. 7,283,217.

(30) Foreign Application Priority Data

Mar. 11, 2004 (JP) ............................. 2004-069098

(51) Int. Cl.
*G01N 33/48* (2006.01)
(52) U.S. Cl. .......................................... 356/39; 356/40
(58) Field of Classification Search ............... 356/39–42
See application file for complete search history.

(56) References Cited

U.S. PATENT DOCUMENTS

| | | | |
|---|---|---|---|
| 4,735,504 A | 4/1988 | Tycko | |
| 5,006,986 A | 4/1991 | Inoue | |
| 5,117,357 A | 5/1992 | Inoue | |
| 5,350,695 A | 9/1994 | Colella et al. | |
| 5,360,739 A | 11/1994 | Fan et al. | |
| 5,411,891 A | 5/1995 | Fan et al. | |
| 5,438,003 A | 8/1995 | Colella | |
| 5,488,469 A | 1/1996 | Yamamoto et al. | |
| 5,821,127 A | 10/1998 | Akai et al. | |
| 5,872,627 A | 2/1999 | Miers | |
| 6,114,173 A | 9/2000 | Zelmanovic et al. | |
| 6,228,652 B1 | 5/2001 | Rodriguez et al. | |

(Continued)

OTHER PUBLICATIONS

"New Red Cell Parameters on the Sysmex XE-2100 as Potential Markers of Functional Iron Deficiency", C. Briggs, et al., Sysmex Journal International vol. 11 No. 2 (2001).

*Primary Examiner*—Michael P Stafira
(74) *Attorney, Agent, or Firm*—Sughrue Mion, PLLC

(57) ABSTRACT

A sample analyzer including a detection unit for irradiating a biological sample with light and obtaining optical information; a cell classification processor for classifying cells contained in the biological sample into cell groups based on the optical information; a scattered light information obtaining processor for obtaining scattered light information relating to a cell included in a predetermined cell group; a calculation processor for calculating a component value corresponding to an amount of component contained in cell included in the predetermined cell group based on the scattered light information; and an output device for outputting the component value calculated by the calculation means is disclosed. A computer program product is also disclosed.

20 Claims, 11 Drawing Sheets

U.S. PATENT DOCUMENTS

| | | |
|---|---|---|
| 6,525,807 B1 | 2/2003 | Morikawa et al. |
| 6,784,981 B1 | 8/2004 | Roche et al. |
| 7,283,217 B2 * | 10/2007 | Ikeuchi et al. .................. 356/39 |
| 7,450,223 B2 * | 11/2008 | Ikeuchi et al. .................. 356/39 |
| 2001/0053551 A1 | 12/2001 | Jiang et al. |
| 2003/0030784 A1 | 2/2003 | Narisada et al. |
| 2003/0032193 A1 | 2/2003 | Narisada |
| 2004/0132196 A1 | 7/2004 | Mizukami et al. |

\* cited by examiner

FIG. 10

| Examination | | |
|---|---|---|
| Items | Data | Unit |
| RBC | 461 | 10^4/uL |
| RBC-O | 453 | 10^4/uL |
| HGB | 12.5 | g/dL |
| HCT | 42.4 | % |
| MCV | 92.0 | fL |
| MCH | 27.1 | pg |
| MCHC | 31.8 | g/dL |
| RDW-SD | 51.5 | fL |
| RDW-CV | 15.2 | % |
| PLT | 25.6 | 10^4/uL |
| PLT-I | 25.6 | 10^4/uL |
| PLT-O | 21.5 | 10^4/uL |
| PDW | 13.0 | fL |
| MPV | 10.9 | fL |
| P-LCR | 32.9 | % |
| PCT | 0.28 | % |
| RET# | 3.46 | 10^4/uL |
| RET% | 0.75 | % |
| IRF | 9.6 | % |
| LFR | 90.4 | % |
| MFR | 8.3 | % |
| HFR | 1.3 | % |
| RET-He | 30.1 | pg |

| Examination items | | |
|---|---|---|
| Items | Data | Unit |
| RET-He | 30.1 | pg |
| RBC-He | 19.0 | pg |
| D-He | 11.1 | pg |
| RET-Y | 1628 | ch |
| RBC-Y | 19.0 | ch |
| IRF-Y | 9.6 | ch |
| RPI | 11.1 | |

| Items | Data | Unit |
|---|---|---|
| FRC# | 3.46 | 10^4/uL |
| FRC% | 0.75 | % |

| Examination items | | |
|---|---|---|
| Items | Data | Unit |
| NRBC# | 0.0 | 10^2/uL |
| NRBC% | 0.0 | /100RBC |

Number: 00717313097  Birth:  Date: 2004/02/03
P.ID: 11111  Sex:  Time: 13:30
Name:
Unit:
Physician:
Comments:

Tabs: Main | Graph | WBC/NRBC | RBC/PLT | Time | Q-Flag | Service | HPC | Research (WBC) | Research (RBC)

Fla: RBC/RET, PLT

RET-EXT, NRBC, PLT, RET, PLT-O, RBC

SAMPLE ANALYZER AND COMPUTER PROGRAM PRODUCT

This is a continuation of application Ser. No. 11/844,522 filed Aug. 24, 2007, which is a continuation of U.S. application Ser. No. 11/076,048 filed Mar. 10, 2005, and now issued as U.S. Pat. No. 7,283,217. The entire disclosures of the prior applications are hereby incorporated by reference.

BACKGROUND OF THE INVENTION

1. Field of the Invention

The present invention relates to a sample analyzer and computer program product, and specifically relates to a sample analyzer and computer program product for analyzing biological samples based on optical information.

2. Background

Analysis of biological samples such as blood and urine is used in the differentiation diagnosis and treatment of disease. Accordingly, blood analyzers which analyze blood using a flow cytometer have been developed for automatic high-speed analysis of many biological samples (refer to U.S. Pat. No. 4,735,504, and U.S. Pat. No. 6,525,807).

Many useful clinical laboratory test items for the differentiation and treatment of disease have been discovered in conjunction with medical advances in recent years. For example, the amount of hemoglobin contained in reticulocytes is used in the differentiation and treatment of anemia. The blood analyzers disclosed in the patent publications above are incapable of obtaining such information.

Non-patent literature has disclosed that parameters (RBC-Y and RET-Y) obtained from histograms of forward scattered light of erythrocytes and reticulocytes are respectively equivalent to the amount of hemoglobin contained in the erythrocytes and reticulocytes (for example, C. Briggs, R. Rogers, B. Tompson, S. J. Machin: New Red Cell Parameters on the Sysmex XE-2100 as Potential Markers of functional Iron Deficiency; Sysmex Journal International; Vol. 11 No. 2:63-68).

Although these parameters correlate with the amount of hemoglobin contained in erythrocytes and reticulocytes, the non-patent literature does not report an analyzer capable of obtaining the amount of hemoglobin contained in erythrocytes and reticulocytes based on these parameters and providing the analysis result to a user.

SUMMARY

The scope of the present invention is defined solely by the appended claims, and is not affected to any degree by the statements within this summary.

An object of the present invention is to increase the number of useful clinical laboratory test items which can be measured by an analyzer.

A first aspect of the present invention is a sample analyzer that comprises a detection unit for irradiating a biological sample with light and obtaining optical information; a cell classification means for classifying cells contained in the biological sample into cell groups based on the optical information; a scattered light information obtaining means for obtaining scattered light information relating to a cell included in a predetermined cell group; a calculation means for calculating a component value corresponding to an amount of component contained in cell included in the predetermined cell group based on the scattered light information; and an output device for outputting the component value calculated by the calculation means.

A second aspect of the present invention is a sample analyzer that comprises a detection unit for irradiating a blood sample with light and obtaining scattered light information and fluorescent light information; a cell classification means for classifying cells contained in the blood sample into a plurality of cell groups including a reticulocyte group based on the scattered light information and fluorescent light information obtained by the detection unit; a reticulocyte group scattered light information obtaining means for obtaining reticulocyte group scattered light information relating to a reticulocyte included in the reticulocyte group; a calculation means for calculating an amount of hemoglobin contained in the reticulocyte based on the reticulocyte group scattered light information; and a display for displaying the amount of hemoglobin calculated by the calculation means.

A third aspect of the present invention is a computer program product for executing a method of analyzing a biological sample, the computer program product comprising computer program code for obtaining optical information from a biological sample irradiated with light; computer program code for classifying cells contained in the biological sample into a plurality of cell groups based on the optical information; computer program code for obtaining scattered light information relating to a cell included in a predetermined cell group; computer program code for calculating a component value corresponding to an amount of a component contained in a cell included in the predetermined cell group based on the scattered light information; and computer program code for outputting the calculated component value.

BRIEF DESCRIPTION OF THE DRAWINGS

FIG. 10 shows an analysis result screen 71 displayed on the display 16 on the terminal side.

DETAILED DESCRIPTION OF THE PREFERRED EMBODIMENTS

The preferred embodiments of the present invention are described hereinafter with reference to the drawings.

The embodiments of the present invention are described below based on the drawings.

An embodiment of the sample analyzer of the present invention is a hemocytometer for analyzing blood and calculating the number of white blood cells (WBC), red blood cells (RBC), and platelets (PLT) and the like.

Figure 1:
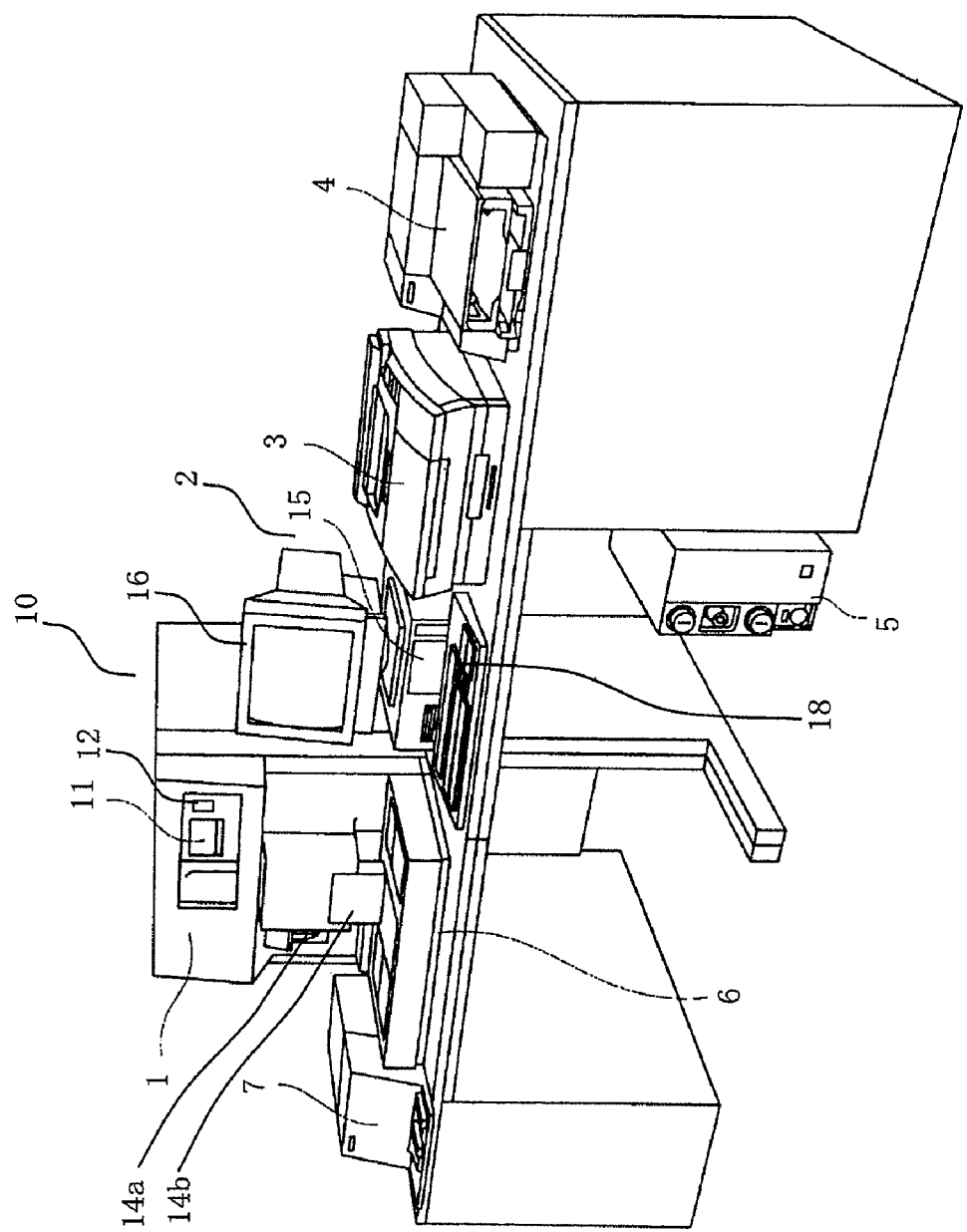
FIG. 1 is a perspective view of the general structure of an embodiment of the sample analyzer of the present invention and peripheral devices.

As shown in FIG. 1, the sample analyzer 10 of the present embodiment includes a device body 1, and data processing terminal 2 connected to the device body 1 through a communication cable (not shown in the drawing).

The device body 1 is connected to a vacuum source 5 for supplying positive pressure and negative pressure to the device body 1 through a tube (not shown in the drawing). The device body 1 is connected to a sampler 6, which automatically transports specimen containers so as to supply samples (blood) to the device body 1. The device body 1 is connected through a tube to a reagent container not shown in the drawing, and suctions reagent from the reagent container using the negative pressure supplied from the vacuum source 5.

The device body 1 is provided with sample suction units 14a and 14b for suctioning blood, a display 11 on the body side which includes a liquid crystal display, and an input unit 12 on the body side which includes a keyboard.

The sample suction unit 14a is used in manual mode to suction blood while the user holds the specimen container, and sample suction unit 14b is used in sampler mode using the sampler 6 to automatically transport sample containers and suction blood.

The data processing terminal 2 includes a terminal body 15, terminal side display 16 which includes a CRT display, and a terminal side input unit 18 which includes a keyboard and mouse not shown in the drawing.

The data processing terminal 2 is connected, by respective communication cables (not shown in the drawings), to a page printer 3 for printing a list of analysis results, a color graphics printer 4 for printing particle distribution diagrams and scattergrams, and a data printer 7 for printing analysis results on form paper.

Figure 2:
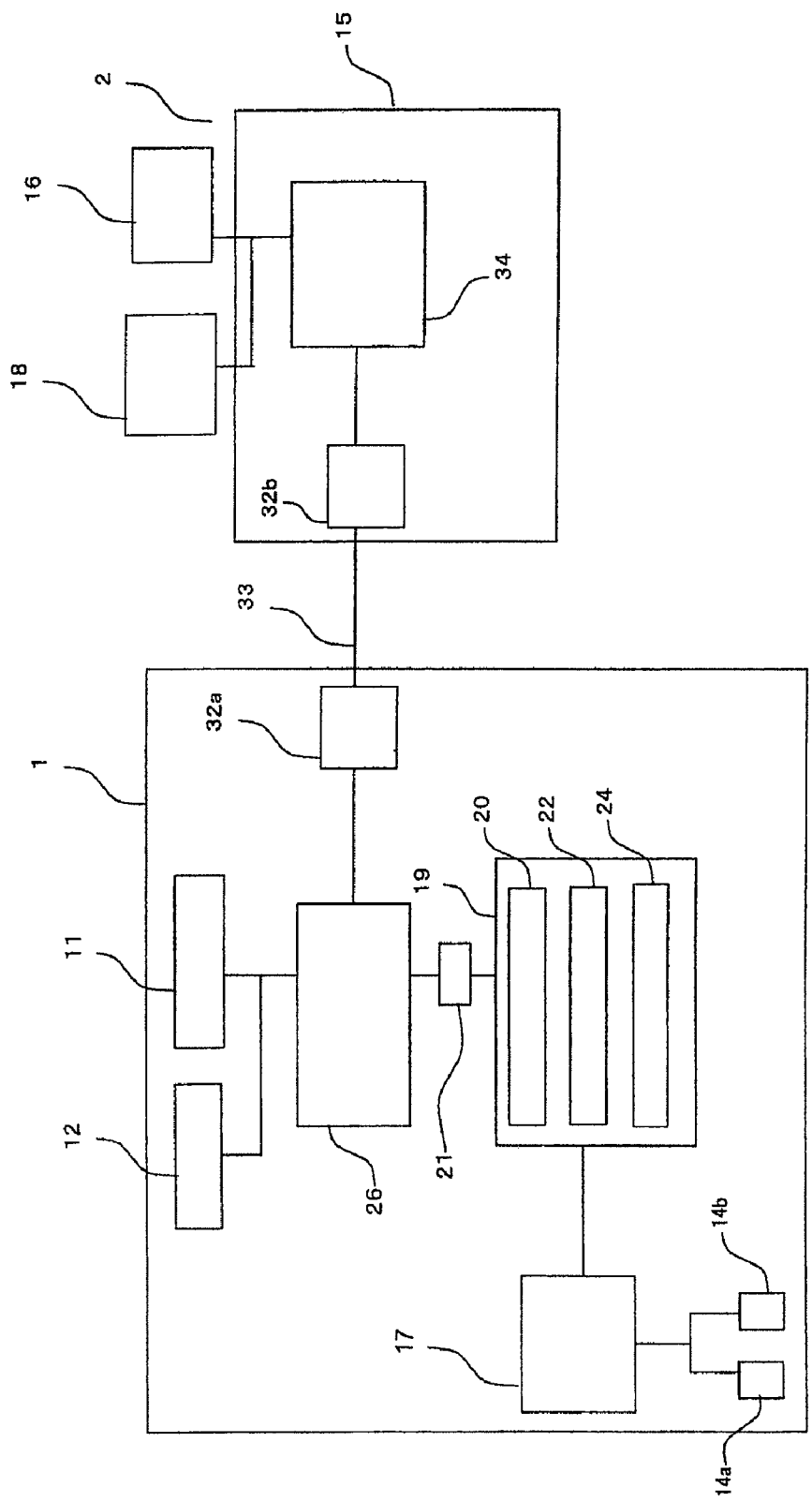
FIG. 2 is a block diagram showing the internal structures of a device body 1 and data processing terminal 2.

As shown in FIG. 2, the device body 1 includes sample suction units 14a and 14b, sample preparation unit 17, detection section 19, A/D conversion circuit 21, body side controller 26, body side display 11, body side input unit 12, and I/O interface 32a.

The sample preparation unit 17 performs processing such as dilution, hemolysis, and staining by mixing the blood suctioned by the sample suction units 14a and 14b and the reagent suction from a reagent container not shown in the drawing. The assay sample prepared by these processes is supplied to the detection section 19. The detection section 19 includes an optical detection unit 20, electrical detection unit 22, and absorbance detection unit 24.

The electrical detection unit 22 includes a sensor using the RF/DC detection method, and a sensor using the sheath flow DC detection method. The sensor described as the 'first measuring part' in the specification of U.S. Pat. No. 6,525,807 may be used as the sensor using the sheath flow DC detection method.

A detection unit including a transparent cell disposed medially to a light-emitting diode and a photoreceptor element may be used as the absorbance detection unit 24. The absorbance detection unit 24 outputs an electric signal representing the transmission light intensity for a dilution fluid alone, and an electric signal representing the transmission light intensity of a hemoglobin assay sample to the A/D conversion circuit 21. These electric signals are subjected to digital conversion in the A/D conversion circuit 21, and are input to the body side controller 26.

The body side controller 26 is mainly a microcomputer which includes a CPU, ROM, RAM and the like. The body side controller 26 calculates the analysis result output from the detection section 19 and input through the A/D conversion circuit 21. For example, the body side controller 26 calculates the hemoglobin (HGB) concentration from the difference between the transmission light intensity (absorbance) output from the absorbance detection unit 24 and input through the A/D conversion circuit 21. Then, the body side controller 26 transmits the calculated analysis result through the I/O interface 32a to the data processing terminal 2. The body side controller 26 stores the operational expressions, described later, which were used in the calculation of the analysis result.

The body side controller 26 controls the operation of the sample suction units 14a and 14b, sample preparation unit 17, detection section 19 and the like. The body side controller 26 receives data input from the body side input unit 12, and displays predetermined information on the body side display 11. Examples of the information displayed on the body side display 11 include the main clinical laboratory test items of the analysis results, error information and the like.

The terminal body 15 includes an I/PO interface 32b, and terminal side controller 34. The I/O interfaces 32a and 32b are connected through a communication cable 33.

The terminal side controller 34 includes a CPU, ROM, RAM, and hard disk and the like. The terminal side controller 34 displays analysis results transmitted from the device body 1 through the I/O interface 32b on the terminal side display 16, and prints the data on the various printers (refer to FIG. 1).

The terminal side controller 34 transmits the data input from the terminal side input unit 18 to the device body 1 through the I/O interface 32b.

Figure 3:
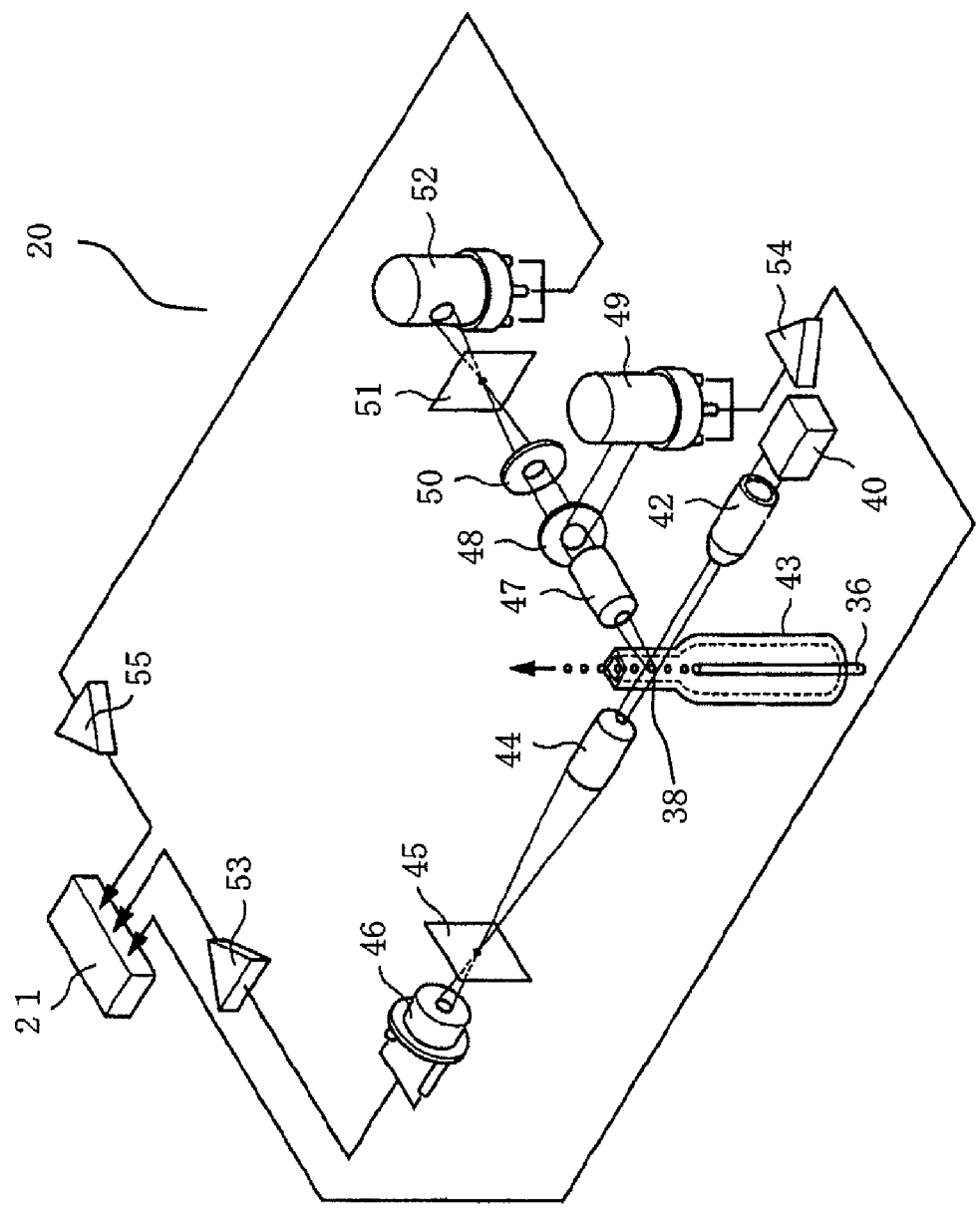
FIG. 3 is a perspective view showing the structure of an optical detection unit 20.

As shown in FIG. 3, the optical detection unit 20 includes a nozzle 36, laser diode 40, collimator lens 42, sheath flow cell 43, condenser lens 44, pinhole plate 45, photodiode 46, condenser lens 47, dichroic mirror 48, photomultiplier tube 49, filter 50, pinhole plate 51, photomultiplier tube 52, and amps 53 through 55.

The assay sample supplied from the sample preparation unit 17 (refer to FIG. 2) flows from the nozzle 36 and through an orifice 38 of the sheath flow cell 43.

Light from the laser diode 40 irradiates the assay sample flowing through the orifice 38 of the sheath flow cell 43 through the collimator lens 42. The light scattered in front of the assay sample flowing through the orifice 38 (forward scattered light) passes through the condenser lens 44 and pinhole plate 45 and enters the photodiode 46.

The light scattered laterally from the assay sample flowing through the orifice 38 (lateral scattered light) enters the photomultiplier tube 49 through the condenser lens 47 and dichroic mirror 48.

The fluorescent light emitted from the assay sample flowing through the orifice 38 (lateral fluorescent light) by the light emitted from the laser diode 40 enters the photomultiplier tube 52 through the condenser lens 47, dichroic mirror 48, filter 50, and pinhole plate 51.

The photodiode 46 outputs an electrical signal which represents the intensity of the input forward scattered light (forward scattered light intensity). The photomultiplier tube 49 outputs an electrical signal representing the intensity of the input lateral scattered light (lateral scattered light intensity). The photomultiplier tube 52 outputs an electrical signal representing the intensity of the input lateral fluorescent light (lateral fluorescent light intensity).

The electrical signals output from the photodiode 46, photomultiplier tube 49, and photomultiplier tube 52 are amplified by the amps 53, 54, 55, respectively, and are input to the A/D conversion circuit 21.

The operation of the sample analyzer of the present embodiment is briefly described below with reference to FIGS. 1 through 10. When a user operates the body side input unit 12 or terminal side input unit 18 to issue instructions to start an analysis operation, the sample suction unit 14a or 14b performs a blood suctioning operation in accordance with the selected operating mode. Then, the sample preparation unit 17 prepares a predetermined assay sample, and the assay sample is supplied to each detection unit of the detection section 19. The optical detection unit 20 respectively outputs electrical signals representing the forward scatter light intensity, lateral scattered light intensity, and fluorescent light intensity to the A/D conversion circuit 21. The electrical detection unit 22 and absorbance detection unit 24 also output electrical signals obtained by detecting the assay sample to the A/D conversion circuit 21. The A/D conversion circuit 21 digitally converts the electrical signals output from the detection section 19, and outputs the data to the body side controller 26. The body side controller 26 analyzes the data and obtains analysis results for the various clinical laboratory test items. Then, the body side controller 26 displays predetermined items from among the analysis results on the body side display 11, and transmits all analysis results to the data processing terminal 2. Then, the terminal side controller 34 of the data processing terminal 2 displays the received analysis results on the terminal side display 16, and stores the analysis results.

The processes of analyzing reticulocytes (RET) and mature erythrocytes using the optical detection unit 20 is described in greater detail below.

When analyzing reticulocytes (RET) and mature erythrocytes, the sample preparation unit 17 dilutes the blood suctioned by the sample suction unit 14a or 14b approximately 200 times, and stains the diluted solution using a predetermined stain. Consequently, a prepared assay sample is supplied to the optical detection unit 20. Then, the optical detection unit 20 irradiates the assay sample with light, and outputs electrical signals representing the forward scattered light intensity, lateral scattered light intensity, and lateral fluorescent light intensity, respectively, to the A/D conversion circuit 21. The A/D conversion circuit 21 subjects the electrical signal output from the optical detection unit 20 to digital conversion, and outputs the data to the body side controller 26. The body side controller 26 analyzes the reticulocytes and mature erythrocytes using the data representing the forward scattered light intensity and lateral fluorescent light intensity among the data output from the A/D conversion circuit 21. The reagents described in U.S. Pat. No. 5,821,127 may be employed as the reagents in the preparation of the sample.

Figure 4:
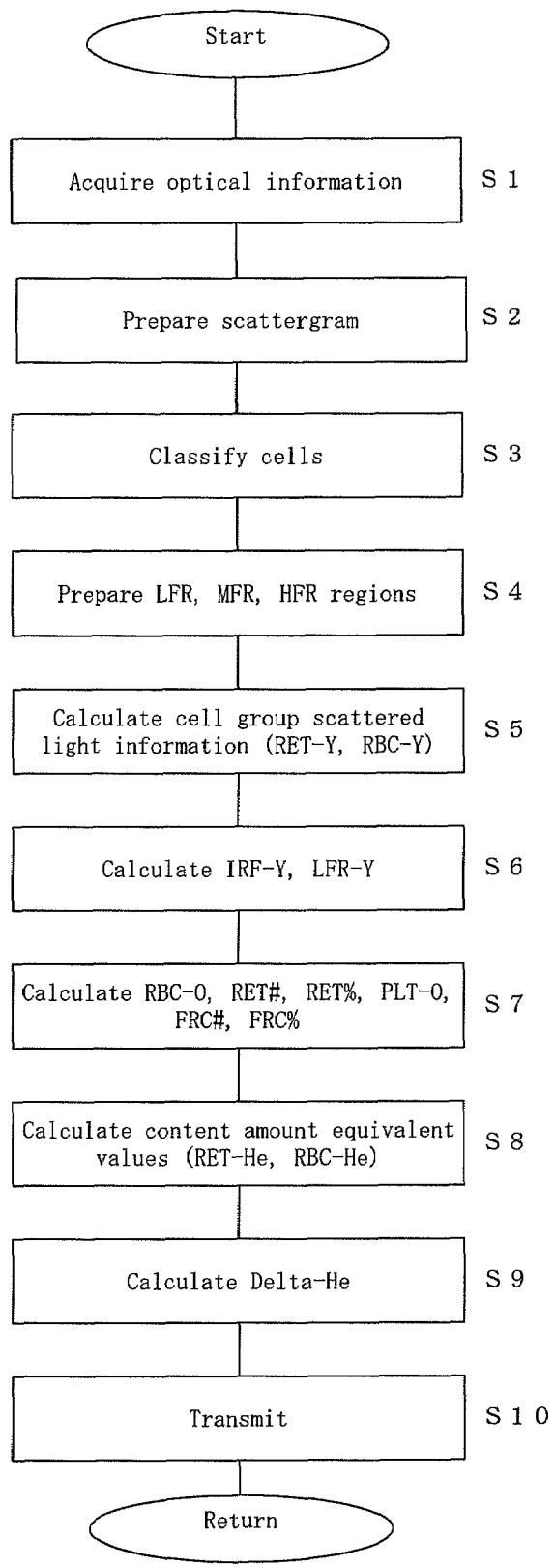
FIG. 4 is a flow chart showing the process of analyzing reticulocytes and mature red blood cells.

The process of analyzing reticulocytes and mature erythrocytes performed by the body side controller 26 is described below using FIG. 4. This process is executed once with a predetermined timing for each measurement of a single sample.

When the data representing the forward scattered light intensity, lateral scattered light intensity, and lateral fluorescent light intensity is transmitted from the optical detection unit 20 and input to the body side controller 26 through the A/D conversion circuit 21, then, the body side controller 26 acquires data in a predetermined period and stores the data representing the forward scattered light intensity and lateral fluorescent light intensity.

Figure 5:
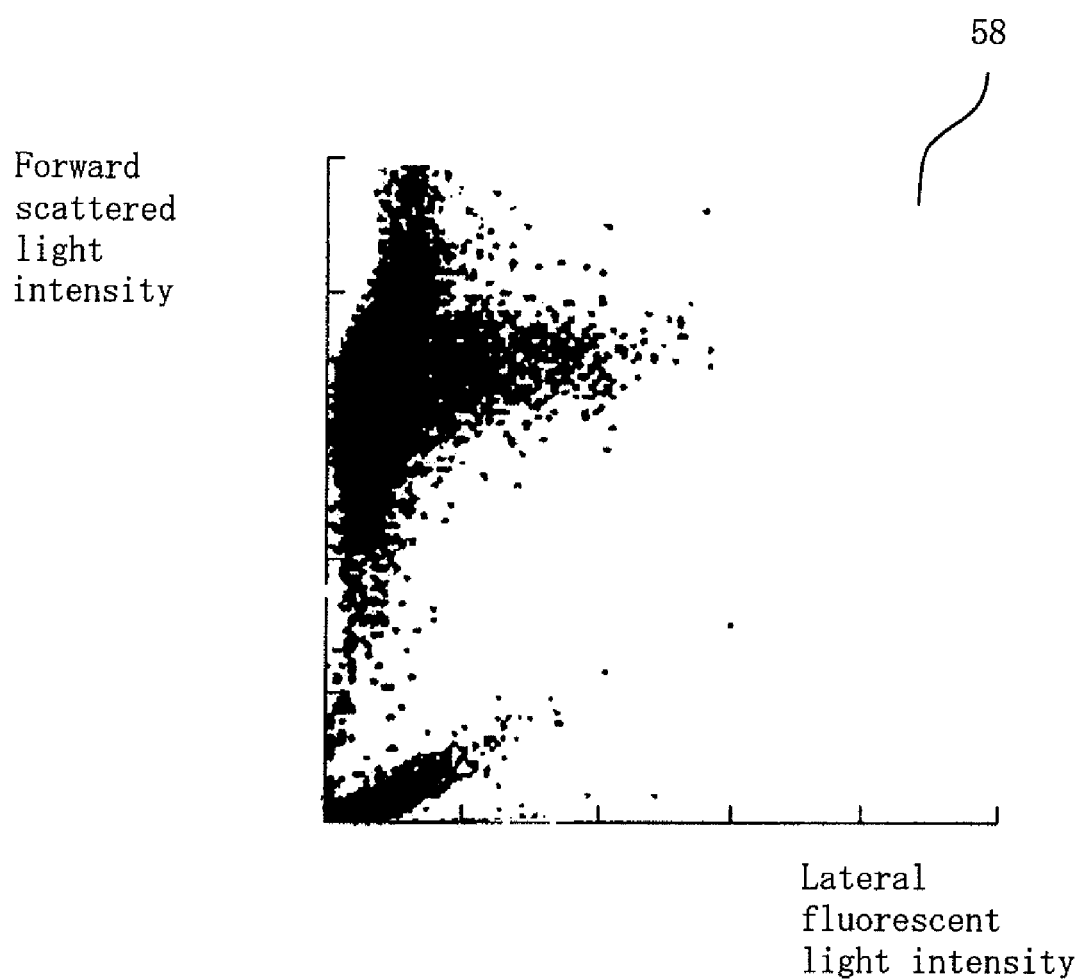
FIG. 5 shows a scattergram 58 stored in the controller 26 on the main body side.

Then the body side controller 26 creates and stores a two dimensional diagram (scattergram) which has the forward scattered light intensity on the vertical axis and the lateral fluorescent light intensity on the horizontal axis based on the stored data representing the forward scattered light intensity and lateral fluorescent light intensity (step S2). The scattergram 58 stored by the body side controller 26 is shown in FIG. 5.

The scattergram 58 is created by extracting individual cells which pass through the orifice 38 based on the data representing the forward scattered light intensity and lateral fluorescent light intensity, determining the forward scattered light intensity and lateral fluorescent light intensity for each extracted cell, and plotting the forward scattered light intensity on the vertical axis and plotting the lateral fluorescent light intensity on the horizontal axis in a two-dimensional diagram for all cells.

Figure 6:
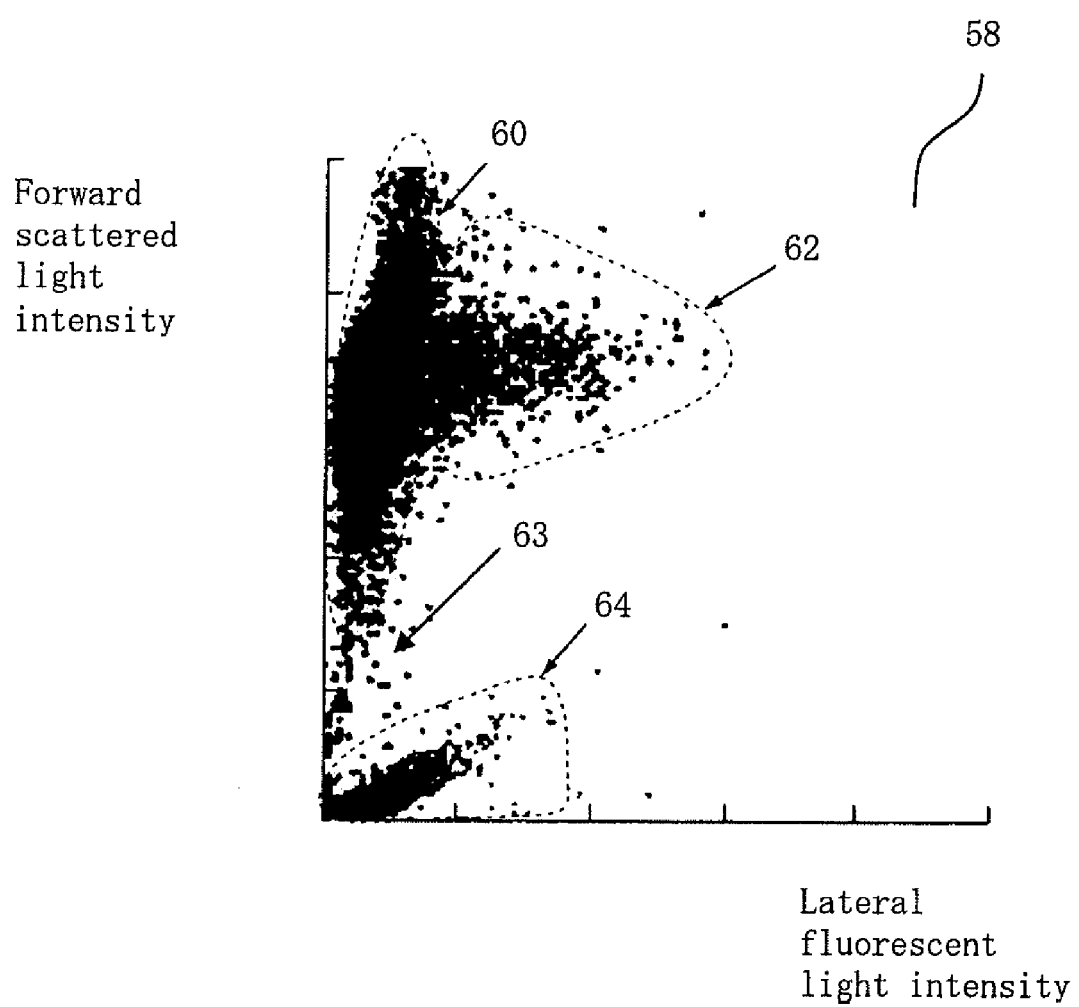
FIG. 6 shows a scattergram 58 stored in the controller 26 on the main body side.
Figure 7:
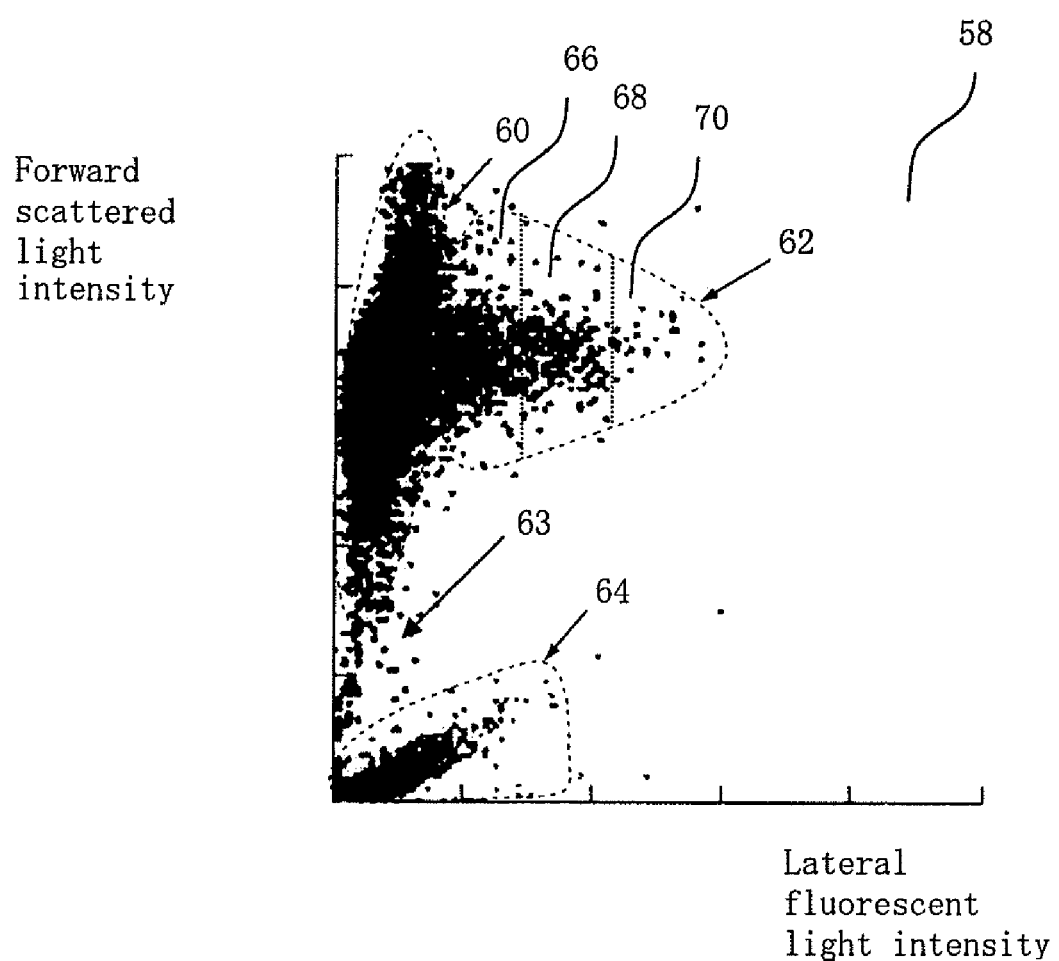
FIG. 7 shows a scattergram 58 stored in the controller 26 on the main body side.

Next, the body side controller 26 classifies and stores the individually extracted cells in cell groups which include the mature erythrocyte group 60, reticulocyte group 62, fragmented erythrocyte group 63, and platelet group 64, as shown in FIG. 6 (step S3).

The mature erythrocyte group 60, reticulocyte group 62, and platelet group 64 can be created, for example, using the methods described in the specifications of U.S. Pat. No. 5,006,986 and No. 5,117,357. Since mature erythrocytes do not contain RNA within the cell, the obtained lateral fluorescent light intensity is extremely low. Since reticulocytes contain RNA within the cell, a comparatively high lateral fluorescent light intensity is obtained. Using these criteria, these methods classify cells which emit a lateral fluorescent light intensity greater than a predetermined amount as reticulocytes. The scattered light intensity obtained by irradiating a cell with light reflects the size of the cell. Since a platelet is smaller than both a mature erythrocyte and a reticulocyte, platelets can be classified separately from mature erythrocytes and reticulocytes.

The fragmented erythrocyte group 63 can be created using, for example, the method described in the specification of U.S. Pat. Publication No. 2001-53551.

The mature erythrocyte group 60, reticulocyte group 62, fragmented erythrocyte group 63, and platelet group 64 may have a fixed range determined beforehand, or the ranges may be modified in accordance with the cell incidence condition on the scattergram.

Next, the body side controller 26 creates and stores trisects the reticulocyte group 62 in accordance with the lateral fluorescent light intensity, and creates and stores an LFR range 66, MFR range 68, and HFR range 70 (step S4).

Since cells which have a high lateral fluorescent light intensity are cells which contain an abundance of RNA produce, it can be stated that reticulocytes which have a high lateral fluorescent light intensity are juvenile reticulocytes. That is, it can be said that reticulocytes in the HFR range 70 are younger than reticulocytes in the MFR range 68, and reticulocytes in the MFR range 68 are younger than reticulocytes in the LFR range 66.

Figure 8:
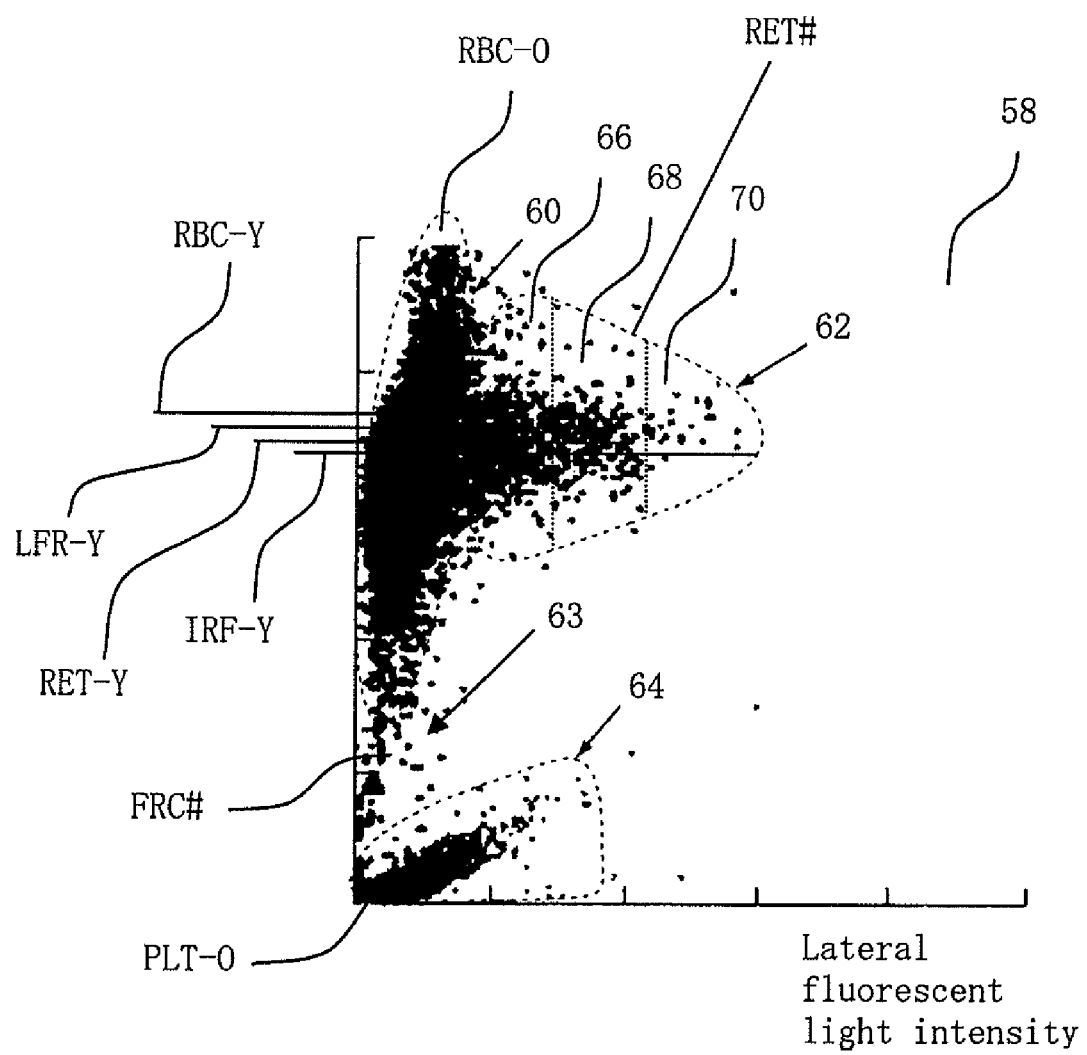
FIG. 8 shows a scattergram 58 stored in the controller 26 on the main body side.

Next, the body side controller 26 calculates and stores the RET-Y and RBC-Y as scattered light information, as shown in FIG. 8 (step S5).

RET-Y is the average value of the forward scattered light intensities of all cells (that is, reticulocytes) included in the reticulocyte group 62.

RBC-Y is the average value of the forward scattered light intensities of all cells (that is mature erythrocytes) included in the mature erythrocyte group 60.

Then, the body side controller 26 calculates and stores the IRF-Y and LFR-Y, as shown in FIG. 8 (step S6).

The IRF-Y is the average value of the forward scattered light intensities of all cells (that is, juvenile reticulocytes) included in the MFR range 68 and HFR range 70. The IRF-Y is a value which reflects the size and hemoglobin content of the juvenile reticulocytes. Accordingly, these values are useful for the differentiation and treatment of anemia.

LFR-Y is the average value of the forward scattered light intensities of all cells (that is, reticulocytes approaching mature erythrocytes) included in the LFR range 66. LFR-Y is a value which reflects the size and hemoglobin content of reticulocytes at the stage of differentiating to erythrocytes. Accordingly, these values are effective in the differentiation and treatment of anemia.

Next, the body side controller 26 calculates and stores the number of cells (mature erythrocytes) RBC-O included in the mature erythrocyte group 60, the number of cells (reticulocytes) RET# included in the reticulocyte group 62, the percentage RET % of the number of cells (number of reticulocytes) included in the reticulocyte group 62 relative to the total number of erythrocytes (number of mature erythrocytes+number of reticulocytes+fragmented erythrocytes), the number of cells (platelets) PLT-O included in the platelet group 64, the number of cells (fragmented erythrocytes) FRC# included in the fragmented erythrocyte group 63, and the percentage FRC % of the number of cells (number of fragmented erythrocytes) included in the fragmented erythrocyte group 63 relative to the total number of erythrocytes (step S7).

Then, the body side controller 26 calculates and stores the RET-He and RBC-He as component value from the RET-Y and RBC-Y calculation results, respectively, stored in step S5 (step S8).

RET-He is calculated using the following equation stored in the body side controller 26. RET-He is equivalent to the amount of hemoglobin contained in the reticulocytes.

$$RET\text{-}He = A \times exp(B \times RET\text{-}Y) \quad \text{Equation 1}$$

(Where A=5.8439, and B=0.0098)

RBC-He is calculated using the following equation stored in the body side controller 26. RBC-He is equivalent to the amount of hemoglobin contained in mature erythrocytes, that is, MCH (mean corpuscular hemoglobin).

$$RBC\text{-}He = C \times exp(D \times RBC\text{-}Y) \quad \text{Equation 2}$$

Where C=5.8439, and D=0.0098)

Then, the body side controller 26 calculates and stores the Delta-He from the RET-He and RBC-He calculation results stored in step S8 (step S9).

Delta-He is calculated by subtracting RBC-He from RET-He.

Then, the body side controller 26 transmits all data stored in steps S1 through S9 to the terminal side controller 34 of the data processing terminal 2 (step S10).

Next, Then, the body side controller 26 ends the reticulocyte and erythrocyte analysis control routine, and starts the analysis control for the other clinical laboratory test items.

Equations 1 and 2 are determined by the following methods.

Equation 2 is obtained by analyzing a plurality of samples beforehand to acquire the forward scattered light intensity of mature erythrocytes (RBC-Y) and MCH (mean corpuscular hemoglobin), and plotting the analysis results in a two-dimensional diagram, to determine the relationship between RBC-Y and MCH.

The specific method of determining equation 2 is described below using FIG. 11.

Figure 11:
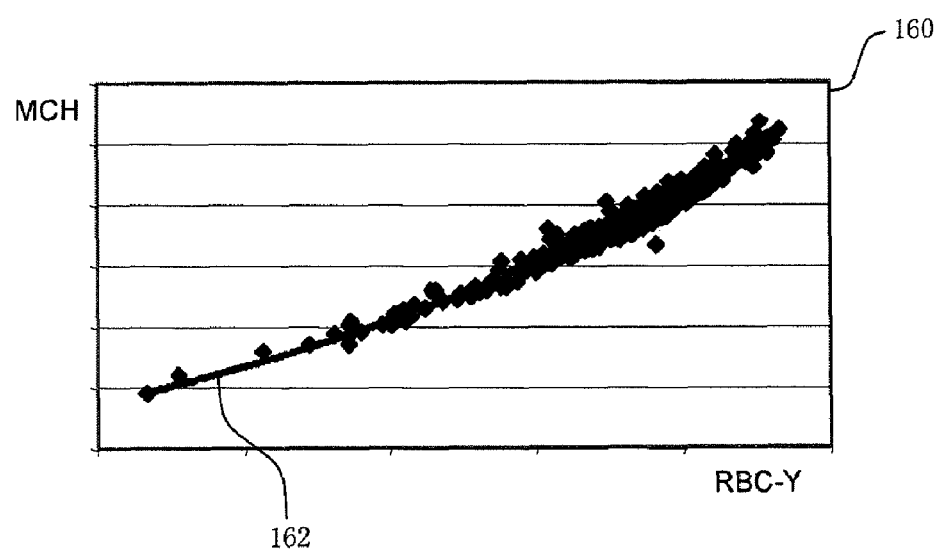
FIG. 11 shows a two-dimensional distribution diagram used for equation determination.

The vertical axis of the two-dimensional distribution shown in FIG. 11 represents the magnitude of MCH, and the horizontal axis represents the magnitude of RBC-Y.

First, approximately 500 specimens were analyzed using the optical detection unit 20 to obtain the RBC-Y. The number of RBC (hereinafter referred to as 'RBC') was then acquired for the same approximately 500 specimens using the electrical detection unit 22, and subsequently the HGB concentration (hereinafter referred to as 'HGB') was acquired using the absorbance detection unit 24.

Then, the MCH was obtained from the acquired RBC and HGB using equation 3 shown below.

$$MCH = (HGB/RBC) \times 1000 \quad \text{Equation 3}$$

Then the analysis results were plotted for these approximately 500 samples, and a two-dimensional distribution diagram 160 was created.

The curve 162 was determined based on the sample distribution in the two-dimensional distribution diagram 160, and the equation representing the curve was calculated. This equation is equation 2 described above, and is used to calculate MCH from RBC-Y.

Equation 1 is determined as described below.

RBC-Y is the average value of the forward scattered light intensities of mature erythrocytes, and MCH is the amount of hemoglobin contained in the mature erythrocytes. Since RET-Y is the average value of the forward scattered light intensities of reticulocytes, if the same calculation is made as the calculation of RBC-He using equation 2, a value can be obtained which is equivalent to the amount of hemoglobin contained in reticulocytes. Therefore, an equation having the same form as equation 2 was used as equation 1 to calculate RET-He. Although MCH is essentially the amount of hemoglobin contained in red blood cells (including both mature erythrocytes and reticulocytes), it is reasonable to consider MCH as the amount of hemoglobin contained in mature erythrocytes since the number of mature erythrocytes contained in peripheral blood is much greater than the number of reticulocytes.

Although equation 1 was determined by the method described above in the present embodiment, it is also possible to determine equation 1 by analyzing a plurality of specimens beforehand to acquire the forward scattered light intensity (RET-Y) of reticulocytes and the amount of hemoglobin contained in reticulocytes, plotting a two-dimensional distribution diagram based on the analysis results, and determining an equation which represents the relationship between the RBC-Y and amount of hemoglobin contained in reticulocytes from the distribution condition in the two-dimensional distribution diagram. The amount of hemoglobin contained in reticulocytes may be acquired, for example using a model ADVIA120 (Bayer Diagnostics, Inc.)

The screens displayed on the terminal side display 16 after the body side controller 26 ends the analysis for all clinical laboratory test items is described below using FIGS. 9 and 10.

Figure 9:
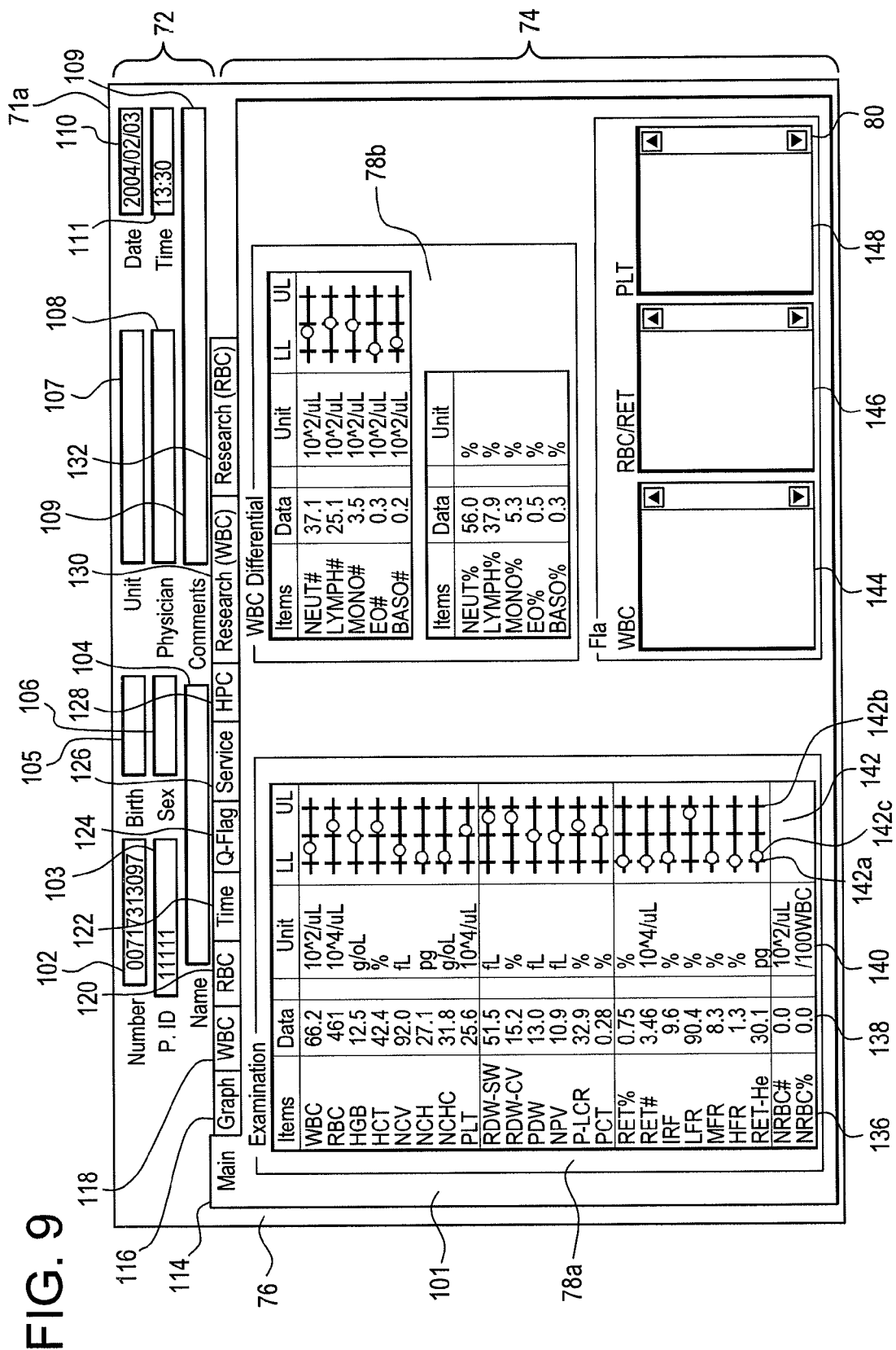
FIG. 9 shows an analysis result screen 71 displayed on the display 16 on the terminal side.

FIGS. 9 and 10 show the analysis result screens displayed on the terminal side display 16 after the body side controller 26 has completed the analysis all clinical laboratory test items. FIG. 9 shows the analysis result screen 71a displayed when the main screen is selected, and FIG. 10 shows the analysis result screen 71b displayed when the research screen (RBC related) is selected.

The analysis result screens 71a and 71b include an specimen information display unit 72 and an analysis result display unit 74.

The specimen information display unit 72 includes a specimen number display 102 for displaying the specimen number of the analyzed specimen (blood), a patient ID display 103 for displaying the identification number of the patient from whom the analyzed specimen was collected, patient name display 104 for displaying the name of the patient, birth date display 105 for displaying the birth date of the patient, sex display 106 for displaying the sex of the patient, ward display 107 for displaying the ward to which the patient is admitted, attending physician display 108 for displaying the attending physician of the patient, comment display 109 for displaying optional comments, assay date display 110 for displaying the date the specimen was analyzed, and assay time display 111 for displaying the time at which the specimen was assayed.

The analysis result display 74 includes a tag display 76, and a screen corresponding to the selected tag is displayed below the tag display 76.

The tag display 76 includes a main tag 114 for displaying the main clinical laboratory test items, graph tag 116 for displaying all the obtained clinical laboratory test items, WBC tag 118 for displaying the clinical laboratory test items related to white blood cells, RBC tag 120 for displaying the clinical laboratory test items related to red blood cells, time series tag 122 for displaying the clinical laboratory test items of specimens collected from a patient in time series, Q-flag tag 124 for displays positive or negative, service tag 126 for displaying predetermined service data, HPC tag 128 for displaying the HPC number obtained by analyzing electrical signals output from the RF/DC detector included in the electrical detection unit 22, research (WBC related) tag 130 for displaying research items related to white blood cells, and research (RBC related) tag 132 for displaying research items related to red blood cells.

Since the main tag 114 is selected in the analysis result screen 71a shown in FIG. 9, a main screen 101 is displayed which shows the main clinical laboratory test items. The main screen 101 includes analysis data displays 78a and 78b, and flag display 80.

The analysis data displays 78a and 78b include an item column 136, data column 138, unit column 140, and normal range column 142.

Names of clinical laboratory test items are displayed in the item column 136, analysis results for each clinical laboratory test item are displayed in the data column 138, the units of the analysis results displayed in the data column 138 are shown in the unit column 140, and the correlation of the analysis result of the analyzed specimen relative to the normal range are displayed in the normal range column 142 (NRBC# and NRBC % are excluded). That is, the normal range column 142 displays a lower limit bar 142a representing the lower limit of the normal range, an upper limit bar 142b representing the upper limit of the normal range, and an analysis result point 142c is positioned so as to make recognizable the correlation of the result with the normal range framed by the lower limit bar 142a and upper limit bar 142b.

Among the clinical laboratory test items displayed on the analysis data displays 78a and 78b, WBC, RET %, RET#, IRF, LFR, MFR, HFR, RET-He, NRBC#, NRBC %, NEUT#, LYMPH#, MONO#, EO#, BASO#, NEUT %, LYMPH %, MONO %, EO %, and BASO % are calculated using the optical detection unit 20. RBC, HCT, MCV, PLT, RDW-SD, RDW-CV, PDW, MPV, and P-LCR are calculated using the electrical detection unit 22. HGB is calculated using the absorbance detection unit 24, MCH and MCHC are calculated using the electrical detection unit 22 and absorbance detection unit 24, and PLT is calculated using the optical detection unit 20 or electrical detection unit 22.

The flag display 80 includes WBC flag display 144 for displaying a flag (message indicating the analysis result is abnormal) related to WBC, RBC/RET flag display 146 for displaying flags relating to RBC and RET, and PLT flag display 148 for displaying flag related to PLT. In the screen shown in FIG. 9, flags are not displayed in these flag displays.

RET-Y and RBC-Y are not displayed in the analysis result screen 71a.

Since the research (RBC related) tag 132 is selected in the analysis result screen 71b shown in FIG. 10, the research (RBC related) screen 151 is displayed as a screen including research items related to red blood cells.

The research (RBC related) screen 151 includes analysis data displays 82a, 82b, 82c, flag display 86, and scattergram/particle distribution diagram display 88.

Names of clinical laboratory test items, analysis results for each clinical laboratory test item and analysis units are displayed in the analysis data displays 82a, 82b, 82c.

RBC, RBC-O, HGB, HCT, MCV, MCH, MCHC, RDW-SD, RDW-CV, PLT, PLT-I, PLT-O, PDW, MPV, P-LCR, PCT, RET#, RET %, IRF, LFR, MFR, HER, RET-He, RBC-He, D-He, RET-Y, RBC-Y, IRF-Y, RPI, FRC#, and FRC % are displayed on the analysis data displays 82a, 82b, and 82c.

As previously mentioned, RBC-O is the number of cells included in the mature erythrocyte group 60, and is an amount equivalent to the number of mature erythrocytes. The sample analyzer of the present embodiment calculates the number of erythrocytes RBC using the electrical detection unit 22, and improves the reliability of analysis results by analyzing the same clinical laboratory test items by two measurement principles.

RBC-He is the amount of hemoglobin contained in mature erythrocytes, that is, a value equivalent to MCH (mean corpuscular hemoglobin). The sample analyzer of the present embodiment calculates MCH using the electrical detection unit 22 and absorbance detection unit 24, and improves reliability of analysis results by analyzing the same clinical laboratory test items by two measurement principles.

PLT-I is the number of platelets calculated using the electrical detection unit 22, and PLT-O is the number of cells contained in the platelet group 64. Among PLT-I and PLT-O, reliability of analysis results is improved by the more reliable higher value as the platelet number PLT.

D-He is the previously described Delta-He.

Since RET-He is a value equivalent to the amount of hemoglobin contained in reticulocytes, the unit pg, which expresses weight, is appended. Consequently, a user can easily comprehend that RET-He is a value associated with an amount.

Similarly, since RBC-He is a value equivalent to the amount of hemoglobin contained in mature erythrocytes, the unit pg, which expresses weight, is appended. Consequently, a user can easily comprehend that RBC-He is a value associated with an amount.

RPI is a value calculated from the analysis results of RET % and HCT (in the present example, 0.75% and 42.4%), and can be used in evaluating the status of production of erythrocytes.

The scattergram/particle distribution diagram display 88 includes scattergrams 90, 92, 94, 96, and particle distribution diagrams 98 and 100.

The scattergram 90 is an enlargement of only the region in which the lateral fluorescent light intensity is low among the scattergrams for analyzing reticulocytes and mature erythrocytes; the forward scattered light intensity is plotted on the vertical axis, and the lateral fluorescent light intensity is plotted on the horizontal axis.

The scattergram 92 includes the regions in which the lateral fluorescent light intensity is low and high in the aforesaid scattergram.

The scattergram 94 is an enlargement of the vicinity of the platelet region in the aforesaid scattergram.

The scattergram 96 is a scattergram created using different assay samples than those assay samples used for analyzing reticulocytes and mature erythrocytes in order to calculate NRBC# and NRBC %.

The particle distribution diagram 98 shows the erythrocyte distribution created using the electrical detection unit 22.

The particle distribution diagram 100 shows the platelet distribution created using the electrical detection unit 22.

The previously mentioned RBC and PLT-I are analysis results obtained by analyzing these particle distribution diagrams.

As shown in FIGS. 9 and 10, RET-He, which is a component value, is displayed on the analysis result screen 71*a* with the main clinical laboratory test items, but RET-Y, which is the average value of the forward scattered light intensities of reticulocytes, is not. However, both RET-He and RET-Y are displayed on the analysis result screen 71*b*. Consequently, this arrangement is useful since the user can quickly know the analysis results of the main clinical laboratory test items using the analysis result screen 71*a*, and also see the analysis results of detailed clinical laboratory test items related to erythrocytes using the analysis result screen 71*b*. These screens can be easily switched using tags.

The clinical significance of analyzing the amount of hemoglobin contained in reticulocytes is discussed below.

Iron-deficiency anemia and anemia occurring as a complication in cases of chronic disease (anemia of chronic disorder: ACD) are representative examples of anemia. Although administration of an iron-containing preparation is very effective in treating iron-deficiency anemia, iron administration is sometimes ineffective in treating ACD.

Accordingly, in treating anemia, iron-deficiency anemia and ACD must be differentiated. Managing the fluctuation in the amount of iron in the blood (ferrokinetics) is effective in making this differentiation. Clinical laboratory tests used in managing ferrokinetics include clinical laboratory tests of serum iron, serum ferritin, soluble transferrin receptor (sTfR) and the like, however, these clinical laboratory tests are not sufficiently sensitive and are expensive.

Since the amount of hemoglobin contained in reticulocytes reflects the iron content of the newly produced reticulocytes, analyzing this amount is effective in ferrokinetics management.

If RET-He is output using the sample analyzer of the present embodiment, a value is obtained which is equivalent to the amount of hemoglobin contained in reticulocytes, ferrokinetics can be managed quickly and inexpensively, and types of anemia can be effectively differentiated.

In recent years administration of recombinant human erythropoietin (rHuEPO) has become widely used as a treatment for renal anemia. Renal anemia is a disease caused by low production and secretion of erythropoietin by the kidneys.

Improvement often does not occur when treating renal anemia by administering rHuEPO. Most frequently the cause is a functional iron-deficient condition brought on by the administered rHuEPO. In such cases iron-containing preparations must be administered in addition to rHuEPO.

Accordingly, it is important to manage ferrokinetics when treating renal anemia, and analyzing the amount of hemoglobin contained in reticulocytes is effective in this regard.

In this case also, if RET-He is output using the sample analyzer of the present embodiment, a value is obtained which is equivalent to the amount of hemoglobin contained in reticulocytes, ferrokinetics can be managed quickly and inexpensively, and renal anemia can be effectively treated.

The Delta-He calculated by the sample analyzer of the present embodiment may be used as an indicator for evaluating erythrocyte production status, and is effective in differentiating and treating anemia.

The embodiment disclosed above has been described by way of examples in all aspects and is not to be considered as restrictive in any sense. The scope of the present invention is expressed by the scope of the claims and not by the description of the embodiment. The present invention may be variously modified insofar as such modification is within the scope and equivalences of the claims.

For example, although LFR-Y which is calculated in step S6 (refer to FIG. 4) is not displayed on the terminal side display 16 in the sample analyzer of the above embodiment, the present invention is not limited to this arrangement inasmuch as LFR-Y also may be displayed on the body side display 11.

In the sample analyzer of the above embodiment, the body side controller 26 may calculate the ratio of RET-Y and RBC-Y, and display the ratio on the terminal side display 16. The ratio of RET-Y and RBC-Y may be used as an indicator for evaluating the erythrocyte production status, and is effective in the differentiation and treatment of anemia.

Although scattered light information is used to calculate values equivalent to contents of reticulocytes and erythrocytes, the present invention is not limited to this arrangement inasmuch as values which are equivalent to the content of other cells, such as lymphocytes and monocytes, also may be calculated and output.

In the sample analyzer of the present embodiment, the body side controller 26 calculates the analysis results, and displays all analysis results on the terminal side display 16, however, the present invention is not limited to this arrangement inasmuch as all analysis results also may be displayed on the body side display 11, and the analysis results also may be calculated by the terminal side controller 34.

Although the average value of the forward scattered light intensities of reticulocytes and the average value of the forward scattered light intensities of mature erythrocytes are used as scattered light information in the sample analyzer of the above embodiment, the present invention is not limited to this arrangement inasmuch as the barycenter or mode value of the forward scattered light intensities of the reticulocytes and mature erythrocytes also may be used as scattered light information.

Scattergrams are created from the forward scattered light intensity and lateral fluorescent light intensity in the sample analyzer of the above embodiment, however, the present invention is not limited to this arrangement inasmuch as scattergrams may be prepared from two types of scattered light intensity (for example, forward scattered light and lateral scattered light), and scattergrams also may be prepared from electrical information (for example, current value, voltage value, and resistance value and the like) and scattered light intensity.

Although the sample analyzer of the above embodiment is provided with a device body 1 and a data processing terminal 2, the present invention is not limited to this arrangement inasmuch as the present invention is also applicable to sample analyzers which incorporate the functionality of the data processing terminal 2 in the device body 1.

Although the present invention is applied to a hemocytometer in the above embodiment, the present invention is not limited to this arrangement inasmuch as the present invention is also applicable to other sample analyzers, such as urine analyzers which analyze cells contained in urine.

Although the present invention is applied to a sample analyzer in the above embodiment, the present invention is not limited to this arrangement inasmuch as the present invention is also applicable to programs for controlling sample analyzers. Furthermore, the present invention is also applicable to computer readable recording media on which such programs are recorded.

What is claimed is:

1. A sample analyzer comprising:
   a detection unit which irradiates a biological sample with light and obtains optical information:
   a cell classifier which classifies cells contained in the biological sample into cell groups based on the optical information, the cell groups comprising a reticulocyte group and a mature erythrocyte group;
   a scattered light information obtainer which obtains first scattered light information relating to reticulocytes included in the reticulocyte group and second scattered light information relating to mature erythrocytes included in the mature erythrocyte group;
   a calculator which calculates a first component value corresponding to an amount of hemoglobin contained in the reticulocytes included in the reticulocyte group based on the first scattered light information, and a second component value corresponding to an amount of hemoglobin contained in the mature erythrocytes included in the mature erythrocyte group based on the second scattered light information, and which processes the first component value and the second component value; and
   an output device which outputs the processed result by the calculator.

2. The sample analyzer of claim 1, wherein the output device comprises a display for displaying a screen which includes the processed result.

3. The sample analyzer of claim 1, further comprising a cell counter which counts the reticulocytes included in the reticulocyte group and the mature erythrocytes included in the mature erythrocyte group.

4. The sample analyzer of claim 3, wherein the output device comprises a display for displaying a screen which includes the processed result, a number of the reticulocytes and a number of the mature erythrocytes.

5. The sample analyzer of claim 1, wherein the detection unit obtains the optical information by detecting scattered light and fluorescent light.

6. The sample analyzer of claim 1, wherein the output device comprises a display which displays a screen which shows the first and second component values and a unit representing weight.

7. The sample analyzer of claim 1, wherein the detection unit includes a flow cell through which passes the biological sample, a light source which irradiates the flow cell with light, and a detector which outputs a signal based on the intensity of scattered light by the irradiation of the biological sample passing through the flow cell with light.

8. The sample analyzer of claim 7, wherein the detection unit includes a second detector for outputting a signal based on the intensity of fluorescent light by the irradiation of the biological sample passing through the flow cell with light.

9. The sample analyzer of claim 1, wherein the first scattered light information is scattered light intensities of the individual reticulocytes and the second scattered light information is scattered light intensities of the individual mature erythrocytes.

10. The sample analyzer of claim 1, further comprising a memory which stores a first operational expression for obtaining the first component value from the first scattered light information and a second operational expression for obtaining the second component value from the second scattered light information.

11. The sample analyzer of claim 1, wherein the output device comprises a display capable of selectively displaying a first screen which includes the first component value and does not include the processed result, and a second screen which includes the first component value and the processed result.

12. A sample analyzer comprising:
    a detection unit which detects cells in a blood sample;
    a cell classifier which classifies cells detected by the detection unit into a plurality of cell groups including a reticulocyte group and a mature erythrocyte group;
    an obtainer which obtains a first amount of hemoglobin contained in the reticulocytes included in the reticulocyte group, and a second amount of hemoglobin contained in the mature erythrocytes included in the mature erythrocyte group, and which processes the first amount and the second amount; and
    a display which displays the processed result by the obtainer.

13. The sample analyzer of claim 12, wherein the detection unit comprises an optical detection unit which irradiates the cells in the blood sample with light and obtains optical information.

14. The sample analyzer of claim 12, wherein the detection unit comprises an electrical detection unit which obtains electrical information.

15. A sample analyzer comprising:
    a detection unit which detects cells in a blood sample;
    a cell classifier which classifies cells detected by the detection unit into a plurality of cell groups including a reticulocyte group and a mature erythrocyte group;
    an obtainer which obtains a first amount of hemoglobin contained in the reticulocytes included in the reticulocyte group, and a second amount of hemoglobin contained in the mature erythrocytes included in the mature erythrocyte group, and which processes the first amount and the second amount;
    a display which displays the processed result by the obtainer; and
    a cell counter which counts the reticulocytes included in the reticulocyte group and the mature erythrocytes included in the mature erythrocyte group.

16. The sample analyzer of claim 15, wherein the output device comprises a display which displays a screen which includes the processed result, a number of the reticulocytes and a number of the mature erythrocytes.

17. The sample analyzer of claim 12, wherein the output device comprises a display capable of selectively displaying a first screen which includes the first amount and does not include the processed result, and a second screen which includes the first amount and the processed result.

18. The sample analyzer of claim 17, wherein the second screen includes the second amount.

19. A computer program product for enabling a computer to execute a method of analyzing a biological sample, the computer program product comprising:
    a computer readable medium; and
    software instructions, on the computer readable medium, for enabling the computer to perform predetermined operations comprising:
    obtaining optical information from a biological sample irradiated with light;

classifying cells contained in the biological sample into a plurality of cell groups based on the optical information, the cell groups comprising a reticulocyte group and a mature erythrocyte group;

obtaining first scattered light information relating to reticulocytes included in the reticulocyte group and second scattered light information relating to mature erythrocytes included in the mature erythrocyte group;

calculating a first component value corresponding to an amount of hemoglobin contained in the reticulocytes included in the reticulocyte group based on the first scattered light information, and a second component value corresponding to an amount of hemoglobin contained in the mature erythrocytes included in the mature erythrocyte group based on the second scattered light information;

processing the first and second component values: and outputting the processed result of the first and second component values.

20. A computer program product for enabling a computer to execute a method of analyzing a biological sample, the computer program product comprising:

a computer readable medium: and software instructions, on the computer readable medium, for enabling the computer to perform predetermined operations comprising:

detecting cells in a biological sample;

classifying the detected cells into a plurality of cell groups including a reticulocyte group and a mature erythrocyte group:

calculating a first amount of hemoglobin contained in the reticulocytes included in the reticulocyte group, and a second amount of hemoglobin contained in the mature erythrocytes included in the mature erythrocyte group;

processing the first amount and the second amount; and outputting the processed result of the first and second amounts.

* * * * *

UNITED STATES PATENT AND TRADEMARK OFFICE
CERTIFICATE OF CORRECTION

PATENT NO. : 7,633,604 B2 Page 1 of 1
APPLICATION NO. : 12/204736
DATED : December 15, 2009
INVENTOR(S) : Yoshiro Ikeuchi et al.

It is certified that error appears in the above-identified patent and that said Letters Patent is hereby corrected as shown below:

On the Title Page: Item 75

To be deleted: "Jo Lissen"

To be replaced with: Jo Linssen

Signed and Sealed this
Twentieth Day of May, 2014

Michelle K. Lee
*Deputy Director of the United States Patent and Trademark Office*